United States Patent [19]

Maurukas

[11] 4,121,905
[45] Oct. 24, 1978

[54] PROCESS FOR PREPARING BIOLOGICAL COMPOSITIONS FOR USE AS REFERENCE CONTROLS IN DIAGNOSTIC ANALYSES

[76] Inventor: Jonas Maurukas, 6823 W. Lake Ave., Elyria, Ohio 44035

[21] Appl. No.: 826,973

[22] Filed: Aug. 22, 1977

[51] Int. Cl.² ............................................. G01N 33/16
[52] U.S. Cl. ................................ 23/230 B; 23/230 R; 252/408
[58] Field of Search .......................... 23/230 B, 230 R; 252/408

[56] References Cited

U.S. PATENT DOCUMENTS

| | | | |
|---|---|---|---|
| 2,664,403 | 12/1953 | Weichselbaum | 252/408 |
| 2,770,602 | 11/1956 | Weichselbaum | 252/408 |
| 3,466,249 | 9/1969 | Anderson | 252/408 |
| 3,629,142 | 12/1971 | Marbach | 23/230 B |
| 3,876,375 | 4/1975 | Maurukas | 23/230 B |

Primary Examiner—R.E. Serwin
Attorney, Agent, or Firm—Joseph Patrick Burke

[57] ABSTRACT

The present disclosure is directed to the preparation of stable aqueous-containing biological compositions capable of use as liquid reference serums in diagnostic chemical analysis using multichannel automated analyzers and having improved storage stability and capable of storage in the liquid state for extended periods of time measured in weeks when stored at 2° to 8° C.; processes for preparing the reference serums and the process of automated analysis utilizing the improved reference serums. The subject materials are prepared by freezing the aqueous-containing labile biologicals rapidly at temperatures ranging from about −20° to about −30° C., removing from about 98 to 99 weight percent of the water therefrom and storing same (as a dehydrated solid) at 2° to 8° C. until desired use. The dehydrated material is then reconstituted by dissolving it in a medium containing from about 20 to about 50 wt. % of an alkylene polyol containing from 2 to 5 carbon atoms with the remainder being water. The thus reconstituted biological compositions can be stored in the liquid state at 2° to 8° C. for periods of 4 to 5 weeks or at −20° C. for months.

13 Claims, No Drawings

PROCESS FOR PREPARING BIOLOGICAL COMPOSITIONS FOR USE AS REFERENCE CONTROLS IN DIAGNOSTIC ANALYSES

The present invention is directed to a process for preparing stable liquid human reference serums containing biological materials, including such biologically active substances as found in blood serum or plasma e.g. enzymes; metabolites; hormones; electrolytes; etc., in a manner which will enable their storage in liquid form at temperatures ranging from about 2° to 8° C. for 4 to 5 weeks or −20° C. for 12 months and permit their direct use as reference standards in instrumental analysis without the necessity for freezing and thawing before use. This invention is also directed to the improved analytical procedures using the compositions thus prepared.

BACKGROUND, AND PREVIOUS ATTEMPTS TO PROVIDE REFERENCE STANDARDS FOR AUTOMATED ANALYSIS

Biologically active substances such as found in serums: like enzymes; hormones; electrolytes and biologically active metabolites, are used widely in the diagnosis of diseases. They are used as reference standards for instrumental automated colorimetric analysis since they contain all or most of the components of the unknown to be analyzed. Once the diagnosing physician is aware of the patient's concentration of components, viz., differences versus normal mean ranges of concentration of such components, the diagnosis can be made more objectively. In their natural form, when separated from their normal biological environment, such biologically active substances are unstable and undergo undesirable changes under the influence of heat, enzyme action, hydrolysis and other influences causing undesirable molecular transformations therein. In the past, several methods of preservation have been utilized for such labile biological products.

One such procedure involves "freeze-drying" of the biological. The freeze-drying procedure essentially involves rapidly reducing the temperature of the aqueous-containing biological followed by dewatering it to a very substantial, if not total, extent at reduced pressures. The freeze-dried biologicals can be stored as a solid for varying lengths of time depending on their composition. Thus, for example such dehydrated control material as blood serum or blood plasma can be stored for 1 to 2 years when stored at 2° to 8° C.

At present dehydrated freeze-dried biological reference control compositions are reconstituted with distilled water shortly before their intended use.

Once reconstituted their shelf life is usually from three (3) to twenty-four (24) hours when stored in liquid form at 2° to 8° C. Length of stability depends on the nature of the biological material. Small biological molecules, e.g., electrolytes, will be among the most stable whereas large molecules, such as enzymes, are among the least stable. Thus acid phosphatase can decompose within the first two hours after reconstitution with water from the freeze-dried dehydrated state whereas sodium and potassium can be stable for several days.

Customarily the unused portion of freeze-dried reconstituted biological control compositions must be either refrozen to solid form or discarded at the end of each working day. The first method of extending storage life is both expensive (energy wise) because refreezing requires temperatures of −20° to −30° C. and time consuming because of the time required for rethawing.

The second method is obviously wasteful and hence expensive. The process of this invention offers an inexpensive, convenient solution to the aforementioned problems.

The present invention extends the useful shelf (storage) life of reconstituted freeze-dried biological reference control compositions economically and permits them to be kept at 2° to 8° C. in the liquid state for periods of four to five weeks thus not only avoiding substantially the instability problems encountered with refrigerator storage (at 2° to 8° C.) of compositions reconstituted in accordance with the prior art but also avoiding the necessity of refreezing to solid form for storage (at −20° C.) and rethawing for use. Significant improvement in the shelf life at 2° to 8° C. of freeze-dried reconstituted biological reference control compositions have been attained and instability arrested in such compositions containing uric acid, glucose, bilirubin, a variety of enzymes, e.g., alkaline phosphatase, etc. using the process improvement of this invention.

PRIOR ART

In general the preparation and use of biological reference control compositions is well documented in the prior art. For example, the following three publications appearing in professional analytical chemistry journals indicate how such compositions are customarily prepared and/or evaluated: Teasdale, P. R. Beamount, D & Pakee, J.; "Dialized pooled serum and control" *Clinica Chemica Acta* 30, 535 (1970); Hanok, A. Kuo, J. "The Stability of a reconstituted serum for the assay of 15 chemical constituents," *Clinical Chemistry*, 14, 58 (1968); and G. N. Bowers, R. W. Burnett & R. B. McComb, "Preparation and use of Human control materials for monitoring precision in Clinical Chemistry;" *Clinical Chemistry*, 21, 1830 (1975).

In my prior U.S. Pat. No. 3,876,375, a process is disclosed for preparing reference control compositions which are storage stable by a sequence involving (1) partial dewatering (removing 20 to 40 wt.% of water) and (2) adding $C_2$ to $C_5$ alkylene polyol to replace water removed.

The present process differs from that of Maurukas U.S. Pat. No. 3,876,375 in two distinct respects (rendering the two processes mutually exclusive one from the other):

(1) The present process requires the biological reference composition to be substantially completely dewatered (about 98 to about 99 wt.% of its original water is removed) and (2) The present process reconstitutes with a composition containing from about 20 to about 50 wt.% of a $C_2$ to $C_5$ alkylene polyol with the remainder being water.

In accordance with the present invention the substantially completely dewatered reference biological can be stored and shipped in its dewatered state thereby saving shipping costs.

COMPOSITIONS

From the compositional viewpoint, the freshly prepared compositions resulting from the process of this invention are not distinguishable by analysis from those described and claimed in Maurukas U.S. Pat. No. 3,876,375. Thus said compositions are comprised in their non-biological components of from about 50 percent to about 80 weight percent water, from about 50 to about 20 weight percent of an alkylene polyol having from 2 to 5 carbon atoms, the remainder being chiefly at least one natural biological material selected from the such exemplary classes as human or animal serum or plasma, enzymes, proteins, hormones, metabolites, etc.

Suitable alkylene polyols which can be used are: ethylene glycol, propylene glycol, butylene glycol, pentanediol and glycerol. The alkylene polyol material preferably is ethylene glycol, but other alkylene polyols can be utilized individually or in admixture with ethylene glycol.

Usually these aqueous-containing biological compositions contain in their non-biological components from about 60 to about 80 weight percent water, from about 20 to about 40 weight percent of an alkylene polyol of the type indicated hereinabove with the remainder being comprised chiefly of the aforementioned biological material.

In some cases it is desirable to employ various combinations of alkylene polyols. Thus it is desirable to employ compatible mixtures of ethylene glycol and/or propylene glycol and glycerol. While glycerol is often superior to ethylene glycol in regard to keeping proteins in solution, it does yield somewhat undesirable increases in viscosity of biological fluids. Since viscous fluids are hard to pump and introduce into certain equipment, e.g., pipettes, tubes, etc., the utilization of ethylene glycol results in low viscosity and at the same time the attainment of a good depression of the freezing point to permit storage at low temperatures in the liquid state. The use of ethylene glycol in concentrations substantially in excess of 33 percent by volume tends to precipitate protein present in such labile biologicals however.

OVERALL PROCESS CONSIDERATIONS

The process of this invention will be illustrated by describing how typical plasma and serum control material is prepared for monitoring precision in clinical chemistry, viz., use as reference serums in analysis upon which diagnoses are based. The procedure followed is that described in *Clinical Chemistry* Volume 21, pp. 1830 et seq. (1975) by Bowers & Co. Publishers.

Residual plasma or serum is collected into a frozen pool ($-5°$ C. to $-20°$ C.) of 25 to 35 liters. The term "residual plasma" as used herein means several thousand hospital patients serum sample; left-over, each from 2 to 5 ml, combined in "pool." The pool is then defrosted (at temperatures of $10°$ C. to $25°$ C. over a period of 10 to 24 hours) and the particulate matter is filtered from the defrosted pool. Biological compounds, e.g., glucose, urea, enzymes, etc., are then added to the pool to achieve the "target arithmetical values" along with stabilizers, e.g., sodium azide, etc., and the thus prepared pool is dispensed into 10 ml. vials (total 2,500), subsequently freeze dried at temperatures ranging from about $-10°$ C. to $-20°$ C. over a 2 to 10 hour time period at reduced pressures (for drying) of from about 20 to about 1 millimeters of mercury and more preferably from about 5 to 10 millimeters of mercury. After drying, the vials are stoppered and stored at temperatures ranging from about $2°$ to $8°$ C.

Commercial controls are prepared in similar fashion. Dehydrated and stopered tubes can then be stored at temperatures ranging from $2°$ C. to $8°$ C. for up to 2 years. In accordance with conventional practice, the dried sample is redissolved in water, alone, and consumed immediately or discarded at the end of the working day. In accordance with acceptable practice only one refreezing of reconstituted serum is allowed, repeated freezing and thawing rapidly changes the quantitative composition of serum controls. Keeping samples frozen is wasteful as is discarding reconstituted ones which are unused the same day or within a day or so of the day on which they are reconstituted.

These wastes are substantially eliminated by the process of the present invention since unused samples can be stored for 4 to 5 weeks at $2°$ C. to $8°$ C. without having to refreeze them. For example, reconstitution of freeze-dried serum with water, alone, yields reference product with 2 days refrigerator storage (approximately $4°$ C.) life for glucose determination compared with 4 to 5 weeks when serum from the same freeze-dried pool is reconstituted with a mixture containing 33 wt.% ethylene glycol in water. Additionally the same ethylene glycol-water reconstituted reference control compositions can be stored at $-20°$ C. without becoming solid, thus eliminating the necessity for time-consuming defrosting. This is a clear advantage in today's busy laboratories.

AUTOMATED ANALYSIS AND USE OF THE STABLE REFERENCE COMPOSITIONS AS ANALYTICAL STANDARDS IN COLORIMETRY

The present demands of clinical investigation on analytical laboratory services reached the point requiring automated clinical chemistry in place of prior manual methods, with their inherent and cumulative analytic errors. Automated procedures have been devised in which the sources of variability have been closely controlled by such means as the substitution of dialysis for protein precipitation, the combination of test fluid and reagents in flowing streams, closely controlled heating and reaction times, and flow-through, double-beam colorimeters coupled with recorders. Exemplary of such automated analytical devices are the commercially available TECHNICON AUTOANALYZERS available from the Technicon Instruments Corporation, Chauncey, New York.

The sequence of operations for automated analysis is similar to that in a manual method and involves measurement of sample, removal of protein, addition of reagents, heating and reaction timing, measurement of color, and calculation of results. The automated system uses a pumping method in which plastic tubing of various internal diameters is alternately compressed and released by a set of rollers which imitate peristaltic action. Since the rollers travel over the tubing at a constant rate, the actual volume of fluid transported depends on the bore of the tubing. Separation of one sample from the next is achieved by insertion of air bubbles into the stream; this also gives some "scrubbing" action which minimizes contamination of one sample by the next. The segmentation of the fluid streams in this manner also permits mixing by passing the stream through a rigid glass helix, mounted horizontally, in which each small portion of fluid is repeatedly tumbled as it passes along the coil.

Separation of protein from the samples is achieved by dialysis. The dialyzer consists of two plates; in one surface of each plate is cut a very accurately machined spiral groove, forming a continuous channel with a semicircular cross-section. When the two plates are secured with their grooved surfaces facing each other and a very thin cellophane membrane separating them, a continuous channel of circular cross-section, divided along its whole length by the membrane, is formed. The total length of the channel is about 87 inches. If serum is flowing in one half of the channel and a reagent or other aqueous fluid in the other half, dialyzable constituents of the serum will pass across the membrane and enter the stream of reagent. Such substances as urea, glucose, creatinine, uric acid, phosphate, calcium, sodium, potassium, and chloride can by this means be removed from serum and the large nondialyzable protein molecules passed away to waste. It should be pointed out that only a proportion of the small molecules and ions is transferred from the sample stream to the reagent stream; but since, within limits, the same proportion of the constituents of a standard solution will also be transferred, the ratio of sample concentration to standard concentration will be maintained. The automated instrument operates on the accurate measurement of this ratio; reactions do not have to be taken to completion, as in the manual procedures, and thus reaction times can be shortened without loss of accuracy.

If the procedure requires a heating or incubation step, this is achieved by passing the mixture of reagent and sample dialysate along a rigid glass helix immersed in a suitable heating bath. The heating or incubation phase is exactly determined by the time taken by the fluids to traverse the coil when they are pumped at a constant rate. The baths are completely enclosed and stirred continuously, permitting accurate temperature control.

The colored solutions resulting from the reaction between the sample dialysate or standard dialysate and the reagents are passed into the flow-type cell of a twin-beam colorimeter which uses narrow band pass filters (about 17 millimicrons). The air bubbles are removed by suitable venting, and the absorbance of the colored solution is converted to an electrical signal by a photocell. A second photocell, previously set to 100 percent transmittance with a potentiometer, serves as a reference. The difference in light absorbance between the two beams is amplified and fed to the recorder, which shows it as a peak on the tracing. Comparison of the height of the peak produced by the sample with that produced by a standard permits calculation of sample concentration.

The increase in demand for accurate chemical analysis of many components of natural body biological fluids led to the development of multichannel automatic analyzers. These machines were also required to be capable of sequential operation in order to handle the large volume of analytical samples to be analyzed. Since each separate analysis (channel) had to be performed colorimetrically in comparison with a standard of known concentration (by independent analysis); the desirability of using a reference liquid containing each of the components sought to be analyzed became apparent. For example, it is present practice to analyze human blood for 17 to 18 components, whose concentrations are reported in units as follows: total protein "T. Protein" (gram percent); albumin (gram percent); calcium "Ca" (milligram percent); phosphorus "P" (milligram percent); cholesterol (milligram percent); uric acid (milligram percent); creatinine (milligram percent); total Bilirubin "T. Bili." (milligram percent); alkaline phosphatase (International units per milliliter); lactic dehydrogenase "LDH" (International units per milliliter); glutamic-oxaloacetic transaminase "GOT" (International units per milliliter); creatinine phosphokinase "CPK" (International units per Milliliter); chloride "Cl" (milliequivalents per liter); carbon dioxide "$CO_2$" (milliequivalents per liter); potassium "K" (milliequivalents per liter); sodium "Na" (milliequivalents per liter); blood urea nitrogen "BUN" (milligram percent); and glucose (milligram percent).

The liquid reference biological standards (serums) produced according to the process of this invention are used in commercially available differential multichannel analyzers based on colorimetry or spectrophotometry by placing said liquid serum (of known concentration for each component by separate independent analysis) into one of the sample vials in the machine permitting it to run through the machine and then hand setting the printer or recorder to the known concentration of each component as revealed by independent analysis. Hence, each standardized component has its own intensity of color or optical density and can serve as a reference standard for each analysis (channel). Once the opacity or shade or intensity of color has been equated with a mathematical unit value of concentration for each component, then analysis of the various unknowns can proceed automatically to yield multichannel analytical print-out results on a large number of unknowns sequentially. The use of the reference serum compositions of this invention constitutes an improvement because it permits use of a stable reference standard having a composition which is very close to that found in the human body.

EXAMPLE

Ten liters of human serum obtained, frozen from collecting stations was thoroughly mixed, strained through several layers of cheese cloth and filtered at a pressure of 25 lbs/inch$^2$.

In order to achieve various target concentration levels for the serum components, the following reagent grade chemicals were added to the serum pool; glucose, lithium carbonate, uric acid, bilirubin, urea, di-sodium phosphate, creatinine, and phosphoric acid. The following enzyme preparations were also added: lactic dehydrogenase (from beef heart), aspartate amino transferase (from beef heart), creatine phosphokinase (from beef heart) and alkaline phosphatase (from plant source).

The pool of 10 liters was dispensed into 10 ml vials producing 1000 vials. It was them frozen to $-20°$ C. to the solid state. From 98 to 99% by weight, of the water present in the vials, was removed under vacuum from the frozen serum. The vials were stoppered under vacuum and stored in the refrigerator at 4° C.

In order to compare the stability of the glycol-water reconstituted serum with the one reconstituted with pure distilled water, sufficient quantity of vials were reconstituted with 33% ethylene glycol-water mixture (v/v) to it's original 10 ml volume. The comparison controls were reconstituted with distilled water only.

The tubes were capped with rubber stoppers and divided into three equal quantities: (a) for storage at room temperature, (b) for storage in the refrigerator at 4° C. and (c) for storage in a freezer at $-20°$ C.

For analysis, one tube was removed from each storage container. The samples were assayed for seventeen components: total protein, albumin, calcium, inorganic phosphorus, cholesterol, uric acid, creatinine, total bilirubin, alkaline phosphatase, creatine phosphokinase, lactic dehydrogenase, aspartate amino-transferase, chloride, potassium, sodium urea nitrogen, and glucose. A commercially available "Hycel 17 Analyzer" (manufactured and sold by "Hycel Inc," Houston, Texas) was calibrated with "Hycel" reference serum and was used for the above mentioned assays. The samples were assayed initially at approximately daily and weekly intervals. As a result of these tests, it was learned that a 33% concentration of ethylene glycol in water was a practical optimum probably due in some part to the fact that the thus reconstituted product had a viscosity similar to human serum.

TABLE 1
(STABILITY OF SERUM AT ROOM TEMPERATURE)

| ANALYTE | INITIAL | 1st | 2nd | 3rd | 4th |
|---|---|---|---|---|---|
| Creatinine mg% | 2.9 | 3.5 | 2.5 | 3.1 | 3.0 |
| Calcium mg% | 10.2 | 9.8 | 9.7 | 8.5 | 8.0 |
| Lactic Dehydrogenase (I.U.) | 175 | 198 | 190 | 187 | — |
| Phosphorus mg% | 6.8 | 6.8 | 7.3 | 7.7 | 8.0 |
| Creatine Phosphokinase (I.U.) | 91 | 70 | 60 | 75 | 50 |
| Triglycerides mg% | 136 | 108 | 154 | 160 | 110 |
| Transaminase (I.U.) | 68 | 75 | 62 | 57 | 40 |
| Alk. Phosphatase (I.U.) | 24 | 31 | 32 | 33 | — |
| Total Bilirubin mg% | 3.6 | 3.4 | 2.9 | 2.4 | — |
| Sodium m Eq/L | 148 | 151 | 154 | 152 | 152 |
| Potassium m Eq/L | 5.6 | 5.2 | 5.5 | 5.5 | 5.6 |
| Chloride m Eq/L | 112 | 110 | 111 | 110 | — |
| Cholesterol mg% | 200 | 185 | 202 | 193 | 200 |
| Uric Acid mg% | 8.0 | 7.7 | 7.7 | 7.7 | 8.0 |
| Total Protein gm% | 6.9 | 6.6 | 7.1 | 7.0 | 6.8 |
| Globulin gm% | 2.7 | 2.7 | 2.8 | 2.6 | 2.7 |
| Urea Nitrogen mg% | 28 | 27 | 27 | 27 | 26 |
| Glucose mg% | 186 | 179 | 181 | 187 | 185 |

TABLE 2
(STABILITY OF SERUM AT 2° to 8° C)

| ANALYTE | INITIAL | 1st | 2nd | 3rd | 4th |
|---|---|---|---|---|---|
| Creatinine mg% | 4.0 | 3.2 | 2.6 | 4.2 | 3.5 |
| Calcium mg% | 9.9 | 10.0 | 10.2 | 10.0 | 9.9 |
| Lactic dehydrogenase (I.U.) | 196 | 200 | 191 | 190 | 200 |
| Phosphorus mg% | 6.7 | 6.5 | 6.5 | 6.5 | 6.7 |
| Creatine Phosphokinase (I.U.) | 97 | 101 | 68 | 73 | 65 |
| Triglyceride mg% | 154 | 98 | 138 | 138 | 140 |
| Transaminase (I.U.) | 73 | 78 | 68 | 68 | 70 |
| Alk. Phosphatase (I.U.) | 25 | 26 | 27 | 27 | 27 |
| Total Bilirubin (I.U.) | 3.7 | 3.7 | 3.7 | 3.6 | 3.2 |
| Sodium m Eq/L | 153 | 149 | 154 | 156 | 154 |
| Potassium m Eq/L | 5.4 | 5.1 | 5.4 | 5.7 | 5.4 |
| Chloride m Eq/L | 108 | 107 | 110 | 107 | 110 |
| Cholesterol mg% | 188 | 187 | 199 | 190 | 188 |
| Uric Acid mg% | 8.1 | 7.5 | 7.6 | 7.7 | 7.5 |
| Total Protein gm% | 6.7 | 6.8 | 6.9 | 6.7 | 6.7 |
| Globulin gm% | 2.8 | 2.7 | 2.7 | 2.6 | 2.7 |
| Urea Nitrogen mg% | 31 | 27 | 28 | 27 | 27 |
| Glucose mg% | 185 | 173 | 178 | 187 | 177 |

TABLE 3
(STABILITY OF SERUM AT −13° to −20° C)

| ANALYTE | INITIAL | 1st | 2nd | 3rd | 4th |
|---|---|---|---|---|---|
| Creatinine mg% | 3.0 | 3.2 | 2.6 | 3.4 | 3.0 |
| Calcium mg% | 10.3 | 10.0 | 10.2 | 10.9 | 10.2 |
| Lactic Dehydrogenase (I.U.) | 180 | 180 | 188 | 184 | 180 |
| Phosphorus mg% | 6.9 | 6.8 | 6.5 | 6.8 | 6.5 |
| Creatine Phosphokinase (I.U.) | 89 | 70 | 68 | 84 | 70 |
| Triglyceride mg% | 111 | 100 | 132 | 134 | 130 |
| Transaminase (I.U.) | 68 | 72 | 70 | 69 | 71 |
| Alk. Phosphatase (I.U.) | 24 | 27 | 24 | 23 | 24 |
| Total Bilirubin (I.U.) | 3.6 | 3.8 | 3.7 | 3.5 | 3.8 |
| Sodium m Eq/L | 148 | 148 | 153 | 151 | 150 |
| Potassium m Eq/L | 5.2 | 5.2 | 5.4 | 5.3 | 5.2 |
| Chloride m Eq/L | 107 | 110 | 111 | — | — |
| Cholesterol mg% | 190 | 190 | 193 | 179 | 180 |
| Uric Acid mg% | 8.0 | 7.5 | 7.5 | 7.3 | — |
| Total Protein gm% | 6.8 | 6.5 | 6.6 | 6.1 | — |
| Globulin gm% | 2.8 | 2.8 | 2.7 | 2.4 | — |
| Urea Nitrogen mg% | 27 | 29 | 28 | 27 | — |
| Glucose mg% | 185 | 182 | 169 | 165 | — |

Compositions prepared as described in this example were tested for stability on refrigerator storage based on the established permissible limits of deviation as shown below in Table 4.

TABLE 4
PERMISSIBLE LIMITS OF DEVIATION

| Component | Normal Range | | 1 | 1 | 8%* | $.5S_R$** |
|---|---|---|---|---|---|---|
| T. Protein | 6.0–8.0 | g% | .2 | .3 | .16 | 0.22 |
| Albumin | 3.5–5.0 | g% | .2 | .2 | .12 | 0.15 |
| Ca | 8.5–10.5 | mg% | .3 | .4 | .16 | 0.04 |
| P | 2.5–4.5 | mg% | .2 | .3 | .16 | 0.23 |
| Cholesterol | 150–300 | mg% | 10.0 | 18.0 | 12.00 | 17.00 |
| Uric Acid | 2.5–8.0 | mg% | .3 | .6 | .44 | 0.57 |
| Creatinine | 0–1.4 | mg% | .1 | .2 | .11 | — |
| T. Bili. | 0.2–1.0 | mg% | — | .2 | .06 | — |
| Alk. Phos. | 30–85 | mU/ml | 5.0 | 8.0 | 4.40 | — |
| CPK | 25–145 | mU/ml | — | 8.0 | 9.60 | — |
| LDH | 100–225 | mU/ml | 16.0 | 16.0 | 10.00 | — |
| GOT | 7–40 | mU/ml | 2.0 | 2.0 | 2.60 | — |
| Cl | 95–105 | meq/l | 3.0 | 4.0 | 0.80 | 0.9 |
| $CO_2$ | 24–32 | meq/l | 2.0 | 2.0 | 0.64 | 0.8 |
| K | 3.5–5.0 | meq/l | .2 | .2 | 0.12 | 0.14 |
| Na | 135–145 | meq/l | 3.0 | 4.0 | 0.80 | 0.5 |
| BUN | 10–20 | mg% | 1.0 | 1.0 | 0.80 | 1.5 |
| Glucose | 65–110 | mg% | 6.0 | 11.0 | 3.60 | 4.5 |

*Ad Hoc Advisory Committee NIH (National Institute of Health) Guidelines for Preparation of Control Materials: Class A reference material guide line "95% confidence interval does not exceed 8% of the 95% normal range"
**Cotlove Harris & Williams. Clin. Chem. 16 1028 (1970) . $5S_R$ "tolerable analytic variability" 1 acceptable deviations listed for two commercial lyophilized products If results obtained on analyses of the reconstituted liquid reference serum are near or within these limits, it can be concluded that the components were stable. Sample turbidity (as examined periodically by visual inspection) presented no analytical problems, viz., the samples remained clear to the stability level indicated.

In addition to plasma and serum, the process of the present invention is useful in extending the useful "shelf-life" (viz., refrigerator shelf-life) of hemoglobin standards; urine controls and other biological reference controls or standards for significant improvements in stability while eliminating the need for refreezing to the solid state after reconstituting.

The stable, liquid, pooled reconstituted reference serum described is suitable for use as a calibration standard or reference control for clinical chemical analyses by both manual and automated analyzers capable of analyzing a plurality of unknown blood or serum samples.

There has been described a process for preparing stable reference serum from human serum and an improved procedure for automated chemical analysis utilizing said serums.

While the invention has been described above chiefly in relation to human blood serum, its applicability to other human or animal biologically active substances, such as found in serums: e.g. enzymes, hormones, electrolytes, and biologically active metabolites used widely in the diagnosis of diseases, both human and non-human, and other naturally occurring biological liquids for use as analytical reference controls or standards, will be appreciated by those skilled in the art.

What is claimed is:

1. A process for preparing stable, liquid, biological reference control compositions for use in analysis of naturally occurring biologically similar unknowns, said compositions being stable at temperatures of about 8° to −20° C. and capable of extended storage in the liquid state at said temperature, comprising A. obtaining a portion of biological materials similar in composition to and containing the same component materials as the unknown to be analyzed;

B. freezing said biological material over a period of about 10 to about 24 hours;

C. removing from about 98 to about 99 weight percent water therefrom to obtain dehydrated solid;

D. storing said dehydrated solid until it is to be used in analysis; and

E. reconstituting said freeze-dried dehydrated solid with an aqueous composition containing from about 20 to about 50 wt. % of at least one alkylene polyol containing from about 2 to about 5 carbon atoms in a concentration substantially equal to the water removed therefrom in C.

2. A process as in claim 1 wherein said alkylene polyol is ethylene glycol.

3. A process as in claim 1 wherein said alkylene polyol is propylene glycol.

4. A process as in claim 1 wherein said alkylene polyol is glycerol.

5. A process as in claim 1 wherein said alkylene polyol is butylene glycol.

6. A process as in claim 1 wherein said alkylene polyol is pentane diol.

7. A process as in claim 1 wherein said biologically similar material is blood serum.

8. A process as in claim 1 wherein the removal of water is conducted while said biologically similar material is frozen at reduced pressures ranging from about 1 to about 10 millimeters of mercury.

9. A process as in claim 8 wherein said reduced pressure ranges from about 5 to about 10 millimeters of mercury.

10. A process as in claim 1 wherein said reconstituting composition of E. contains from about 20 to about 35 wt. % of said alkylene polyol.

11. A process as in claim 10 wherein said alkylene polyol is ethylene glycol.

12. In a process for performing analyses on unknown biologically active naturally occurring materials, the improvement which comprises employing the stable, liquid, reconstituted composition of claim 1 as a reference control for comparison as a standard conducting the colorimetric analyses utilizing said reference control composition wherein said reference control composition contains the same component materials as said unknowns.

13. In a process for performing automated multichannel analysis on unknown biologically active human blood serum, the improvement which comprises employing the stable, liquid, reconstituted composition of claim 2 as a reference control in standardizing the automated analyzer and thereafter conducting multichannel analyses on human blood serum unknowns containing the same component materials as said reference control composition.

* * * * *